(12) United States Patent
Good et al.

(10) Patent No.: US 9,833,067 B2
(45) Date of Patent: Dec. 5, 2017

(54) HOLDING ARRANGEMENT FOR PACKAGES

(71) Applicant: Svenska Good AB, Floda (SE)

(72) Inventors: Anders Good, Floda (SE); Per Oscarsson, Hälleviksstrand (SE)

(73) Assignee: Svenska Good Medical AB, Floda (SE)

( * ) Notice: Subject to any disclaimer, the term of this patent is extended or adjusted under 35 U.S.C. 154(b) by 0 days.

(21) Appl. No.: 14/778,584

(22) PCT Filed: Feb. 18, 2014

(86) PCT No.: PCT/SE2014/000020
§ 371 (c)(1),
(2) Date: Sep. 19, 2015

(87) PCT Pub. No.: WO2014/148967
PCT Pub. Date: Sep. 25, 2014

(65) Prior Publication Data
US 2016/0278518 A1  Sep. 29, 2016

(51) Int. Cl.
*A47B 55/02* (2006.01)
*A47K 10/18* (2006.01)
(Continued)

(52) U.S. Cl.
CPC .............. *A47B 55/02* (2013.01); *A47F 5/01* (2013.01); *A47K 10/185* (2013.01); *A61B 42/40* (2016.02)

(58) Field of Classification Search
CPC .......... A47F 5/01; A47F 5/0823; A47F 5/083; A47F 5/13; A47F 5/0031; A47F 5/0025;
(Continued)

(56) References Cited

U.S. PATENT DOCUMENTS 2,560,896 A     7/1951  Rubenstein
2,743,020 A  *  4/1956  Rubenstein ............. A47F 7/148
                                                    211/106

(Continued)

OTHER PUBLICATIONS

Sweden Patent and Registration Office, Int'l Search Report in PCT/SE2014/000020, dated Jun. 11, 2014.

*Primary Examiner* — Patrick Hawn
(74) *Attorney, Agent, or Firm* — Piedmont Intellectual Property

(57) ABSTRACT

A holding arrangement has a frame connected to a mounting element for vertically mounting the arrangement, and one or more holding elements on the frame for receiving and retaining packages. Each holding element has a first section that supports a side of a package, a second section that supports a bottom of the package, and a front section that is substantially parallel to the plane formed by the second section and that supports a side of the package provided with an opening. The first and second sections form an angle of substantially 90 degrees, and the second section forms an angle exceeding 100 degrees with a rear plane of the frame. A package can be positioned in each holding element so that its side with the opening is positioned in an upwardly, outwardly inclined plane with respect to the rear plane or a vertical plane of a mounted holding arrangement.

17 Claims, 8 Drawing Sheets

(51) Int. Cl.
*A47F 5/01* (2006.01)
*A61B 42/40* (2016.01)

(58) Field of Classification Search
CPC ......... A47F 5/08; A47F 7/148; A47K 10/185; Y10S 248/905; A47B 55/02; A61B 42/40
USPC .......................... 211/88.01, 88.02, 106, 59.2
See application file for complete search history.

(56) References Cited

U.S. PATENT DOCUMENTS

| | | | |
|---|---|---|---|
| 2,944,679 A | 7/1960 | Rubenstein | |
| 3,089,597 A * | 5/1963 | Kaplan | A47K 10/185 221/46 |
| 3,528,558 A * | 9/1970 | Williams, V | A47F 5/0025 211/126.1 |
| 3,595,404 A * | 7/1971 | Goldstein | A47F 5/0031 211/106 |
| 4,248,352 A * | 2/1981 | White | A47F 5/0823 211/106 |
| 4,694,966 A * | 9/1987 | Sorenson | A47F 5/01 211/106 |
| 4,813,535 A * | 3/1989 | Radocha | A47F 5/0823 206/362 |
| 5,195,643 A * | 3/1993 | Rocco | A47F 13/085 211/181.1 |
| 6,431,375 B2 * | 8/2002 | Spencer | 211/106 |
| 6,564,950 B1 | 5/2003 | Holm | |
| 7,617,941 B2 * | 11/2009 | Colin | A47F 5/13 206/503 |
| 7,784,625 B2 * | 8/2010 | Burgess | A47B 46/005 211/85.15 |
| 9,044,107 B2 * | 6/2015 | Golden | A47F 5/01 |
| 2013/0270292 A1 * | 10/2013 | Sporre Thorburn | A47K 10/18 221/283 |

* cited by examiner

HOLDING ARRANGEMENT FOR PACKAGES

TECHNICAL FIELD

The present invention relates to a holding arrangement for packages according to the first part of claim 1.

BACKGROUND

Different kinds of holding arrangements for packages, which often consist of cardboard boxes or similar and which contain products, particularly disposable articles such as disposable gloves of for example latex, masks etc. are known. Use of such articles is particularly common within medical care where clean, hygienic articles often are a requirement, but they are also used in many other different situations where the requirements as to hygienic and clean conditions are high, for example in many different laboratory environments, within food industry and for production of products where the requirements are particularly high on the products being clean, free from contamination, free from dust or similar. Also in order to protect the user against subjects which can be harmful, bacteria etc. the use of such in packages stored articles, is very common.

Different problems relate to the holding of packages for such articles. It is required that the packages be easily accessible, that it is simple to remove one or a desired number of articles without more articles being withdrawn, since they cannot be put back into the package due to the requirements that the packages be clean or hygienic. Other in the package remaining articles, should also not be affected in such a way that they become incorrectly positioned in the package and difficult to remove from the package in a proper manner, or become dirty or contaminated. This in turn poses high requirements on holding arrangements for such packages. They must admit that packages can be kept in a safe and stable manner, that they are easily accessible and that the storing enables fulfilment of relevant requirements related to hygiene, otherwise in a serious case a consequence may be that bacteria are spread and remaining articles are contaminated and/or that the package itself gets contaminated, and in a less serious case remaining articles have to be disposed of if there is a risk that more articles then intended are removed, which however in turn easily may have as a consequence that they are put back into the package, in particular if many articles unintentionally are withdrawn.

Many holding arrangement are such that it is more or less necessary to, for example with one hand keep the package in place in the holding arrangement, whereas, with the other hand an article is withdrawn through the opening of the package. This among other things means that the package is gripped by hands which are not clean or hygienic and the relevant requirements become difficult to meet in addition to the fact that it is unpractical to have to use both hands.

WO 0 074 530 shows a holder for packages for gloves which is intended for wall mounting. This holder comprises units functioning as springs arranged to load a package from above, in a side plane which is perpendicular to the plane in which the opening of the package is located, in order to in such a manner solve problems with the package being displaced or that it falls out when an article is removed. This retaining is however not sufficient and it has shown that removal of an article easily has as a consequence that one or more articles are withdrawn and fall down for example on the floor, partly due to the opening being located in a vertical plane, partly due to the retaining capacity being unsufficient. Articles which have been touched have to be disposed of, which results in an unnecessary waste, but in the worse case the articles are left, or they are put back into the package, which means that the requirements on cleanness or hygienic conditions are not fulfilled, but that all, or a plurality of, articles in the package are affected. A common way of preventing such a situation is to hold on the package and also hold the article located on the top and which is to remain in the package, which also means that requirements on hygiene or cleanness cannot be fulfilled.

Moreover the articles are not easily accessible, partly due to the construction of the holder as such, and at least to the same extent due to the use of the springy units, which also often require that two hands be used.

SUMMARY OF THE INVENTION

It is therefore an object of the present invention to provide a solution to one or more of the above mentioned problems, and to provide an arrangement through which one or more of the problems can be solved.

A particular object is to provide an arrangement which facilitates the maintaining of high demands on cleanness and hygiene at the same time as it is easy to withdraw articles out of a package opening of a package located in the holding arrangement.

A particular object is to reduce the risk of other articles being withdrawn, or affected, being displaced or similar, when one article is withdrawn.

Another object is to provide a holding arrangement capable of holding packages in place in such a way that it becomes possible to withdraw articles using but one hand, without the package being tilted, articles unintentionally being withdrawn, and this independently of the filling degree of the package.

It is also an object to provide an arrangement which is easy and cheap to fabricate, which is compact and, in addition thereto is durable.

A further particular object is to provide an arrangement which is environment friendly, which shows advantages as far as storing and transportation are concerned, and which preferably is recycleable.

Another particular object is to provide an arrangement which is flexible and easy to mount. Still another particular object is to provide an arrangement which admits a facilitated access to articles in the package as compared to hitherto known arrangements, and which is ergonomic in use.

It is also a particular object of the invention to provide a holding arrangement which can be made and adapted for use with varying needs concerning size, desired amount of packages to be stored in the holding arrangement, available space for positioning of the holding arrangement etc.

Therefore a holding arrangement as initially referred to is provided, which has the characterizing features of the characterizing part of claim 1.

Advantageous embodiments are given by the characteristic features of the dependent claims.

BRIEF DESCRIPTION OF THE DRAWINGS

The invention will in the following be further described, in a non-limiting manner, and with reference to accompanying drawings, in which.

DETAILED DESCRIPTION

Figure 1:
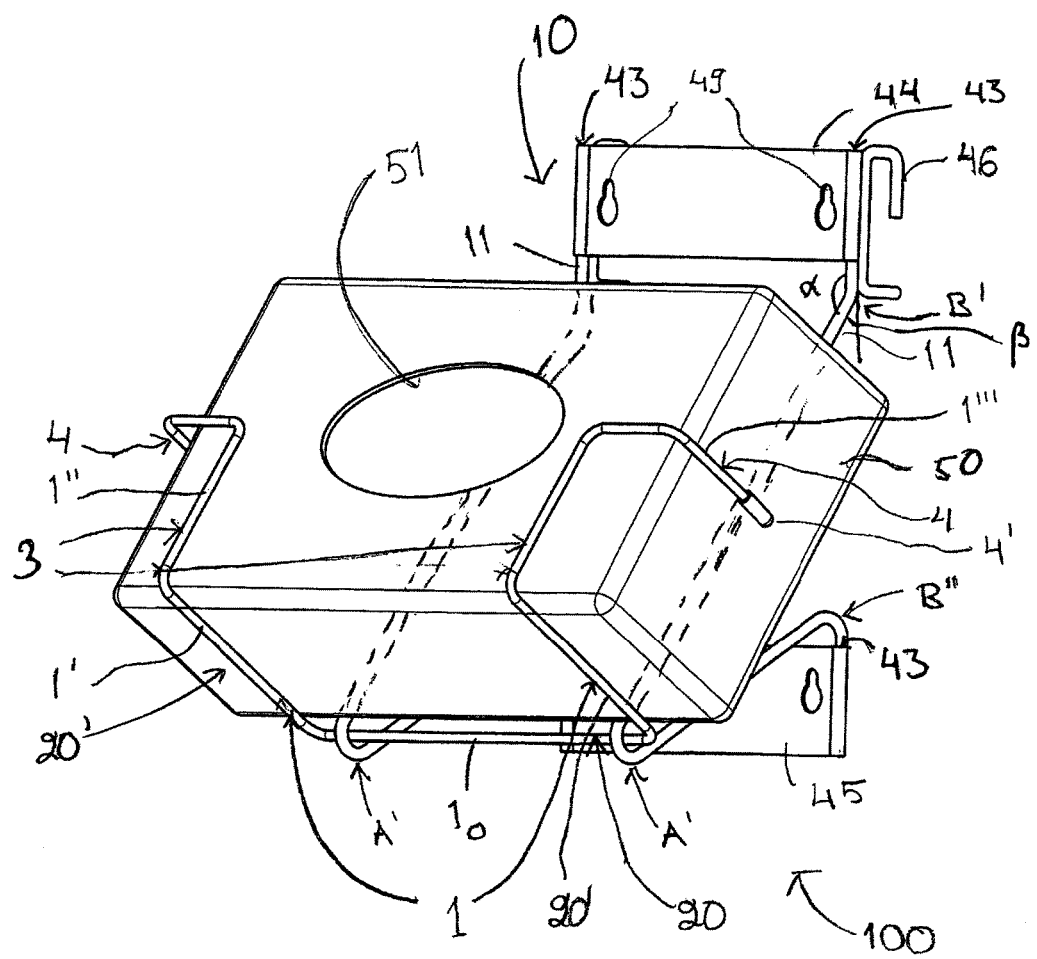
FIG. 1 shows, in perspective, a first embodiment of a holding arrangement according to the invention.

FIG. 1 shows a holding arrangement 100 having a frame structure comprising two parallel frame elements 11, 11 extending in parallel in a substantially vertical direction when the holding arrangement is in a mounted state. In the shown embodiment the frame elements 11, 11 at their upper ends are mounted (for example detachably introduced into grows 43 in the mounting element or fixedly connected thereto) at an upper mounting element 44 for example for mounting on a wall, here by the use of screws (not shown) introduced into therefor arranged openings in the mounting element 44. The mounting element can be formed in any appropriate way for connection to a wall, a rim, a bed etc. In the shown embodiment the mounting element has a dual functionality and comprises also, or is, fixedly or detachably, connected to, a separate mounting element 46 for mounting on a rail or a ramp intended for equipment for intensive care, a so called IVA rail. According to different embodiments of the invention the mounting element may either comprise a simple mounting element for mounting for a particular application, or two or more of the elements mounted on the frame structure adapted for different functionalities, fixedly or replaceably, or in one piece, or of a combined mounting element for several functionalities.

In an embodiment which is not shown, the upper outer ends of the frame elements 11, 11 are inclined downwards instead of upwards as in FIG. 1, and are located in same plane as, and pointing in the same direction as, lower ends of the frame elements, and may for example simply be introduced into grows 43 in respective mounting elements arranged for example on a wall vertically above each other, which enables simple mounting of the holding arrangement.

For example, the lower mounting element may be mounted on a wall, the lower free ends of the frame elements can be introduced into grooves 43, upper mounting elements can be mounted at upper free ends of the frame elements 11, and thereupon the upper mounting element can be screwed for example onto a wall. Of course mounting can take place in the reverse order, with the upper mounting element mounted for example on a wall first, or in any other desired manners. The holding arrangement may of course also be formed as an integral unit or in any other desired manner.

In the shown embodiment the frame elements 11, 11 have free lower ends (here denoted lower since after mounting of the holding arrangement they will be located in its lower part), which are mounted at, mountable at, or in one piece with, a lower mounting element 45. The frame structure 10 here comprises two frame elements 11, 11 with said upper and lower end portions extending in or terminating in, one and the same plane, forming a rearplane (for example in a mounted position, in, or in parallel with, a wall plane).

The frame elements here comprise a wireshaped material of metal, particularly preferably of stainless steel, but also other materials are of course possible to use.

In ends opposed to the free upper, outer ends of the upper ends portions the frame elements (the wire elements) are angled, at rear support points B', B' to form an angle $\alpha$ with the rear plane which exceeds 100°, preferably is between 120° and 160°, or in some cases up to 170°, even more preferably is between 130° and 155°, and even more particularly is between about 142° and 155°.

Inclined in such an angle, or forming an angle $\beta$, which is a complementary angle of the angle $\alpha$, with a rearplane or a wall plane or a plane parallel with the wall plane, where the arrangement is to be arranged in a mounted state, the frame elements 11, 11 extend a distance which is a part of and forms a bottom support section 2 which is intended to form a bottom support for the bottom side of a package 50, i.e. the side of the package which is opposite to the side of a package being provided with an opening 51.

After said distance the frame elements 11, 11 are here angled, in folding points A', A', and extend in a direction towards the rearplane, whereupon they, in said plane, at lower, rear support points B', B' in the same plane as the rear support points B", B" again are angled, to turn into the lower end sections or the outer end portions, which extend in parallel in the rearplane, or in any convenient manner are mounted at the lower mounting elements or element 45 in the rear plane.

The holding arrangement 100 comprises in the in FIG. 1 shown embodiment a holding element 20 which here comprises a bent wire shaped element, preferably of stainless steel. The holding element 20 comprises a bent wire with two parallel side branches 20', 20' which form a first lower support section 1 which extends in a plane which is perpendicular to the plane in which the bottom support section 2 extends, i.e. perpendicularly to the bottom support section 2. The two side branches comprise two first branch sections 1', 1' which are interconnected by means of an interconnecting branch $1_0$, in this example perpendicularly arranged with respect to the two first branch sections 1', 1'. The plane which is formed through the side sections 1', 1' and the interconnecting branch $1_0$ thus form the lower support section 1 which is perpendicular with respect to the bottom support section 2. After, here, a 90° bend of the first branch sections, these turn into second branch sections 1", 1" which are arranged to form a front support section 3. The front branch sections 1", 1" are arranged to be in contact with the upper side of a package 50 being provided with an opening 51 placed in the holding element 20.

In the shown embodiment the front branch sections 1", 1" after, here a bend of 90° in the plane, and a further bend of 90° in a direction towards the rear plane, turn into third side branch sections 1''', 1''' forming side support sections 4, 4. The angles between the first, the second and the third branch sections can take other, different values, as far as the lower, first branch sections 1', 1' delimit or are located in a plane 1 which forms substantially 90° with the bottom support plane 2, the second branch sections are located in or delimit a plane which is substantially in parallel with the bottom support plane 1, and the third branch section are located in parallel planes which are perpendicular to these planes. In some embodiments, see for example FIG. 5 below, the side support sections can be dispensed with.

Through the use of wire elements (the flexibility can also be provided for through elements which are formed in different manners, for example sheet spring steel or some other band shaped element) and since the third frame sections have free outer ends, the holding elements will become partly flexible and resilient in a lateral direction, which means that the holding element will be adaptable to different widths of packages. By using spring steel the flexibility can also be achieved transversally, here with respect to package thickness.

In the shown example the holding element 20 is connected to the frame section 1 in such manner that the interconnecting branch 1$_0$ is attached, for example welded, in the folding points A, A (which particularly form 90° angles) on the rearside of the frame structure in these points. These angles can of course be larger as well as smaller than 90°.

Figure 2:
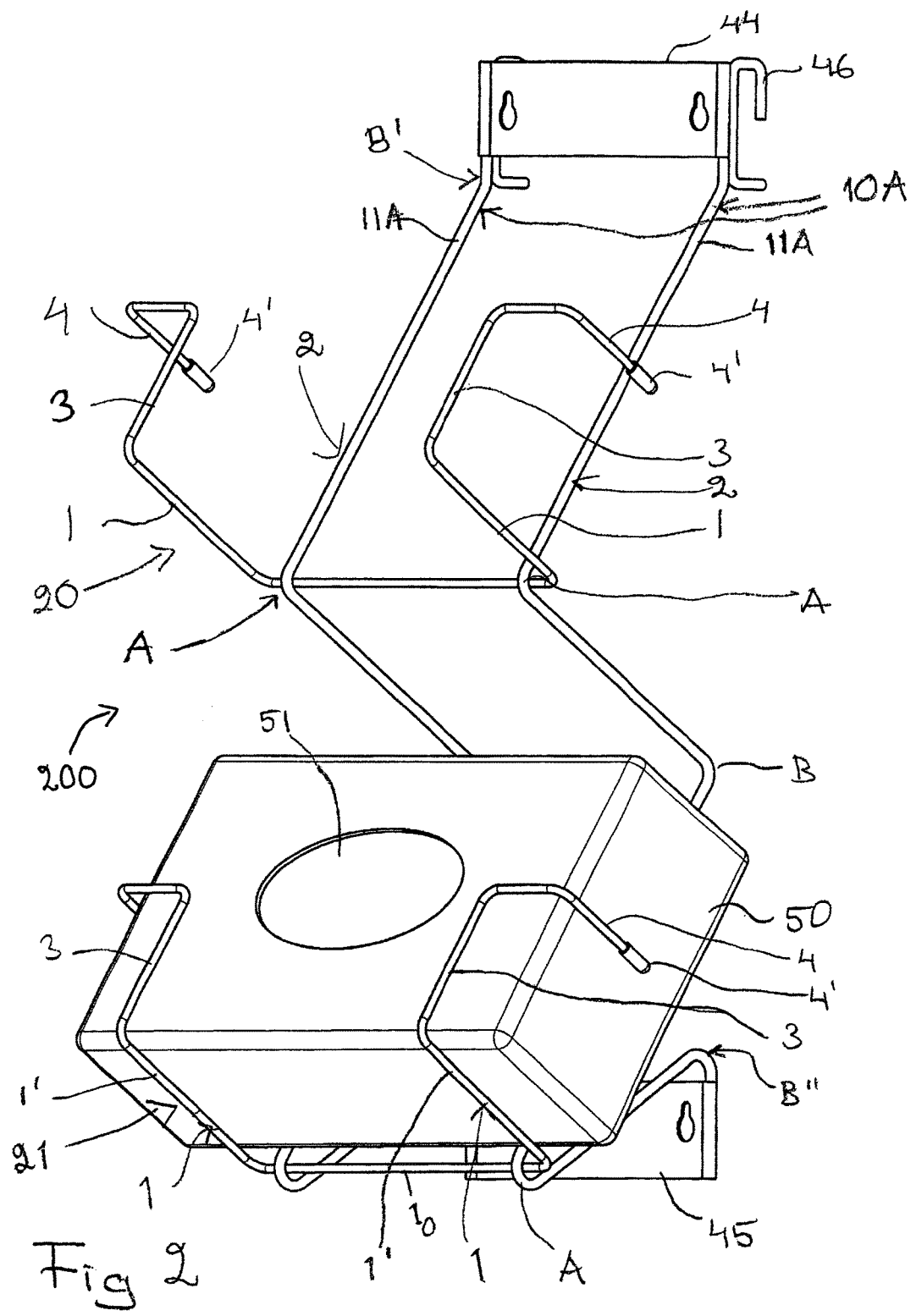
FIG. 2 shows a second embodiment of a holding arrangement according to the invention.

FIG. 2 shows a holding arrangement 200 which comprises two holding elements 20, 21 which each correspond to the holding element 20 which is described with reference to FIG. 1, and therefore will not be further described here. The frame structure 10A substantially corresponds to the frame structure in FIG. 1, but it is extended and comprises intermediate folding point A and intermediate rear support point B, so that instead two bottom support sections 2, 2 are formed which, in a mounted state, are vertically arranged with respect to one another so that two packages can be arranged vertically, one above the other so that their, with openings provided sides will be located in an upwards, outwards sloping position which makes it very easy to withdraw an article.

The inclination, which is relevant for all embodiments, is such that it will both be easier to grip an article, and therefore will be possible to arrange the holding arrangement at lower height, since the openings of the packages through the inclination both will be easily accessible from above and be visible. The holding arrangement 200 may in other respects be varied in corresponding manners as described with reference to FIG. 1.

In an alternative, not shown, embodiment, the holding arrangement can be so formed that it, in the same holding element can take up two next to each other arranged packages which then will be so arranged that their long sides are located adjacent to each other, particularly one and the same holding element optionally can be used for one or two packages. Then should, however, the inclination be less (i.e. the angle β be smaller, in some cases down to 10°), and preferably, but not necessarily, those sections of the frame elements 11, 11 which are to form the bottom support section, be longer.

The first frame sections 1', 1' (the lower support section 1) of the holding element 20 (when it forms a holding element which is not the lowermost in the shown embodiments, extends to form an extension of a plane which is formed by the frame elements 11, 11 between folding points A, A and the rear support points B, B.)

Figure 2A:
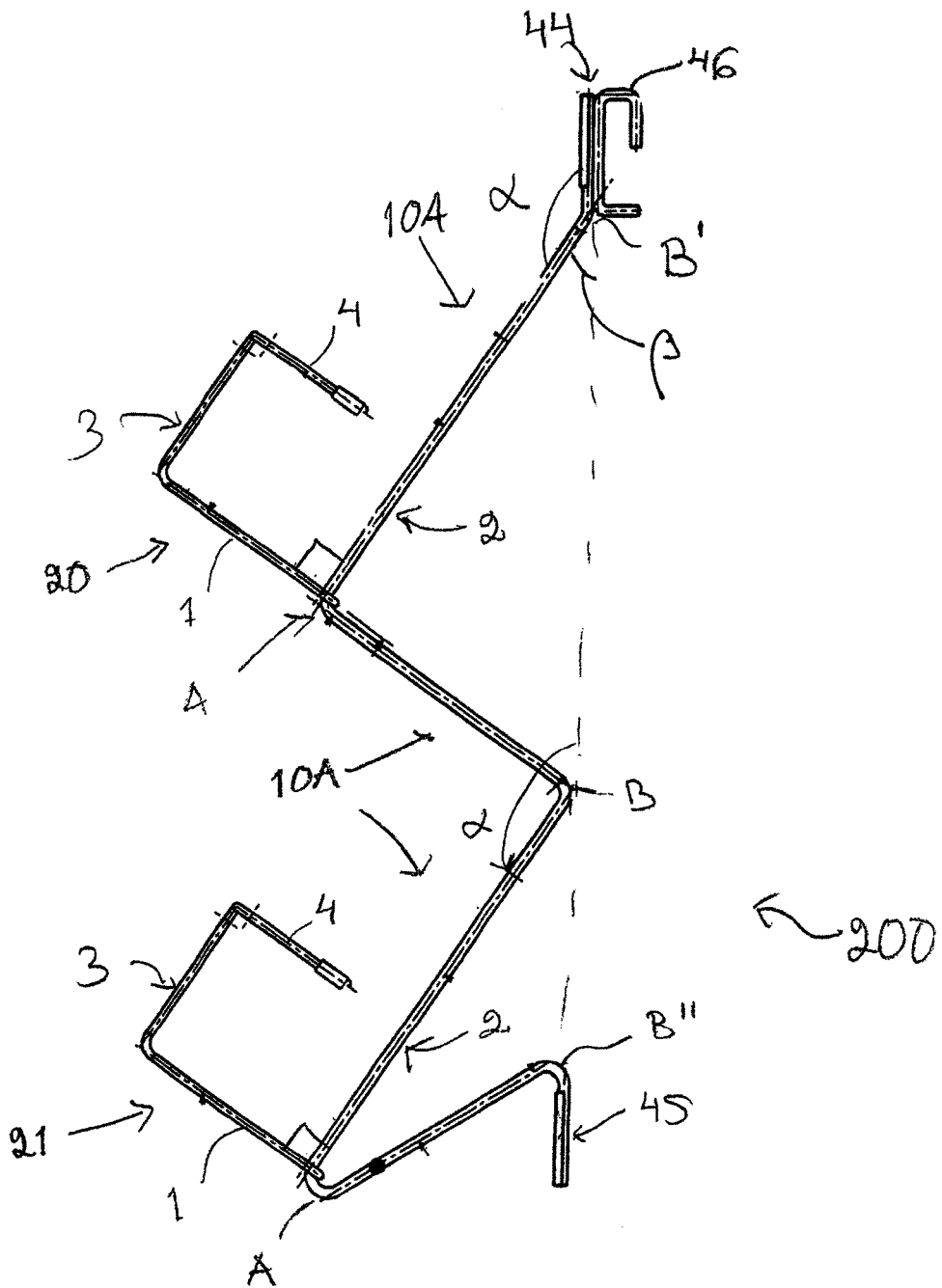
FIG. 2A is a side view of the holding arrangement in FIG. 2.

FIG. 2A is a side view of the arrangement 200. The rear plane is dashed in FIG. 2, the angle α is indicated between respective bottom support section 2, 2 (the bottom support planes which are formed by sections of the two frame sections between the rear support points B', B och the folding points A, A') and said rear plane.

In FIG. 2A are also shown the, preferably, straight angles (which in some embodiments can be adapted to the shape of the package to be held) between respective bottom support section 2, 2 and respective lower support section 1, 1. The outer ends of the free frame sections 4, 4 are here provided with outer protectors of plastic or similar; this is of course not necessary, but they may also be without any protection whatsoever or they can be bent in an appropriate manner, for example form circle or similar, so that no sharp edges are formed.

Figure 3:
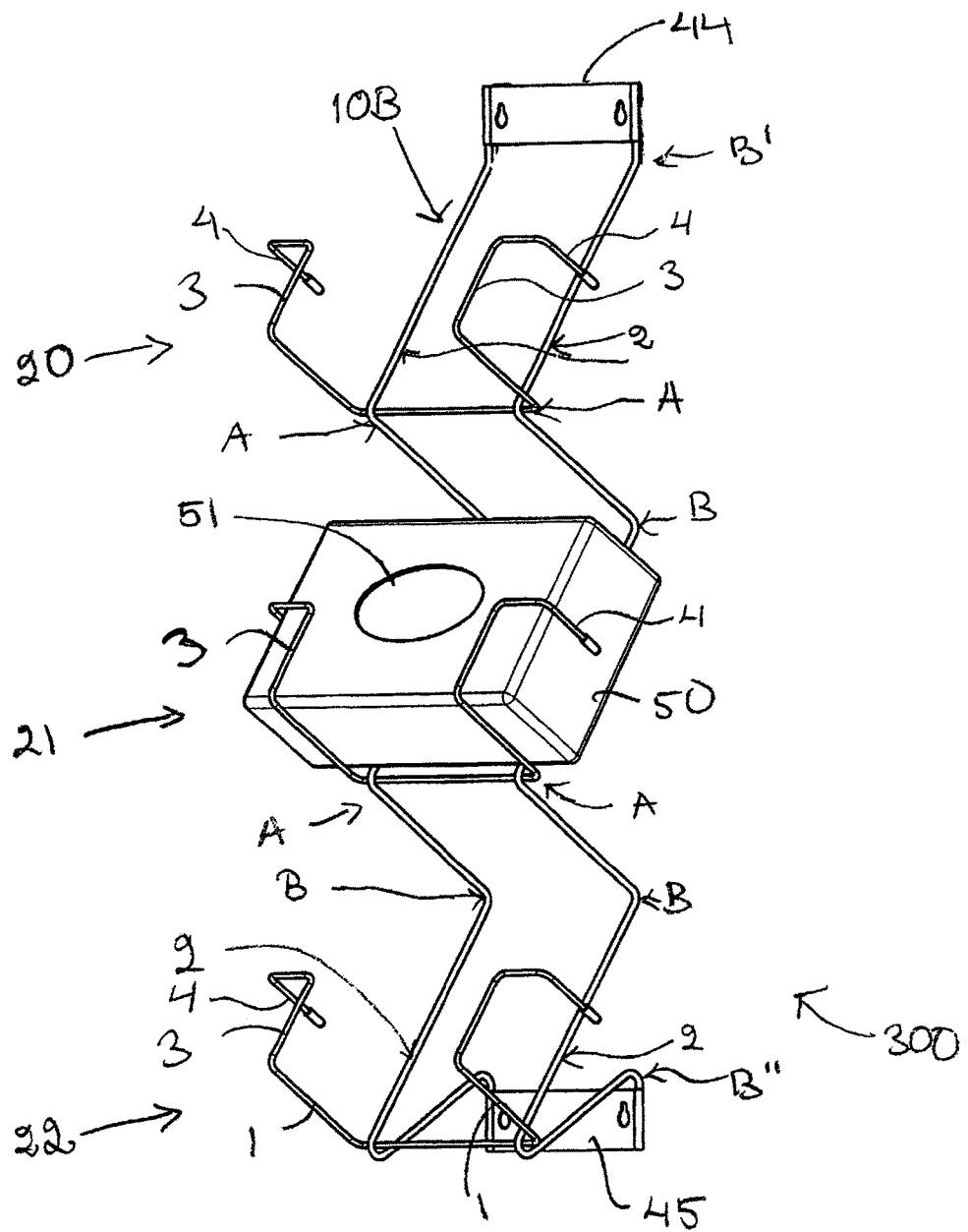
FIG. 3 shows a further alternative embodiment of a holding arrangement according to the invention.

FIG. 3 shows a holding arrangement 300 which corresponds to the one shown with reference to FIG. 2, with the difference that the frame structure 10B is longer and that it comprises three holding elements 20, 21, 22 which in a mounted state of the holding arrangement are located vertically one above the other. In addition thereto, the upper mounting element 44 in this example is adapted exclusively for wall mounting, i.e. the arrangement here does not comprise a combined mounting element for wall mounting or for mounting for example on a ramp. It should however be clear that in this example as well as in the other embodiments many different types of mounting elements can be used.

Figure 4:
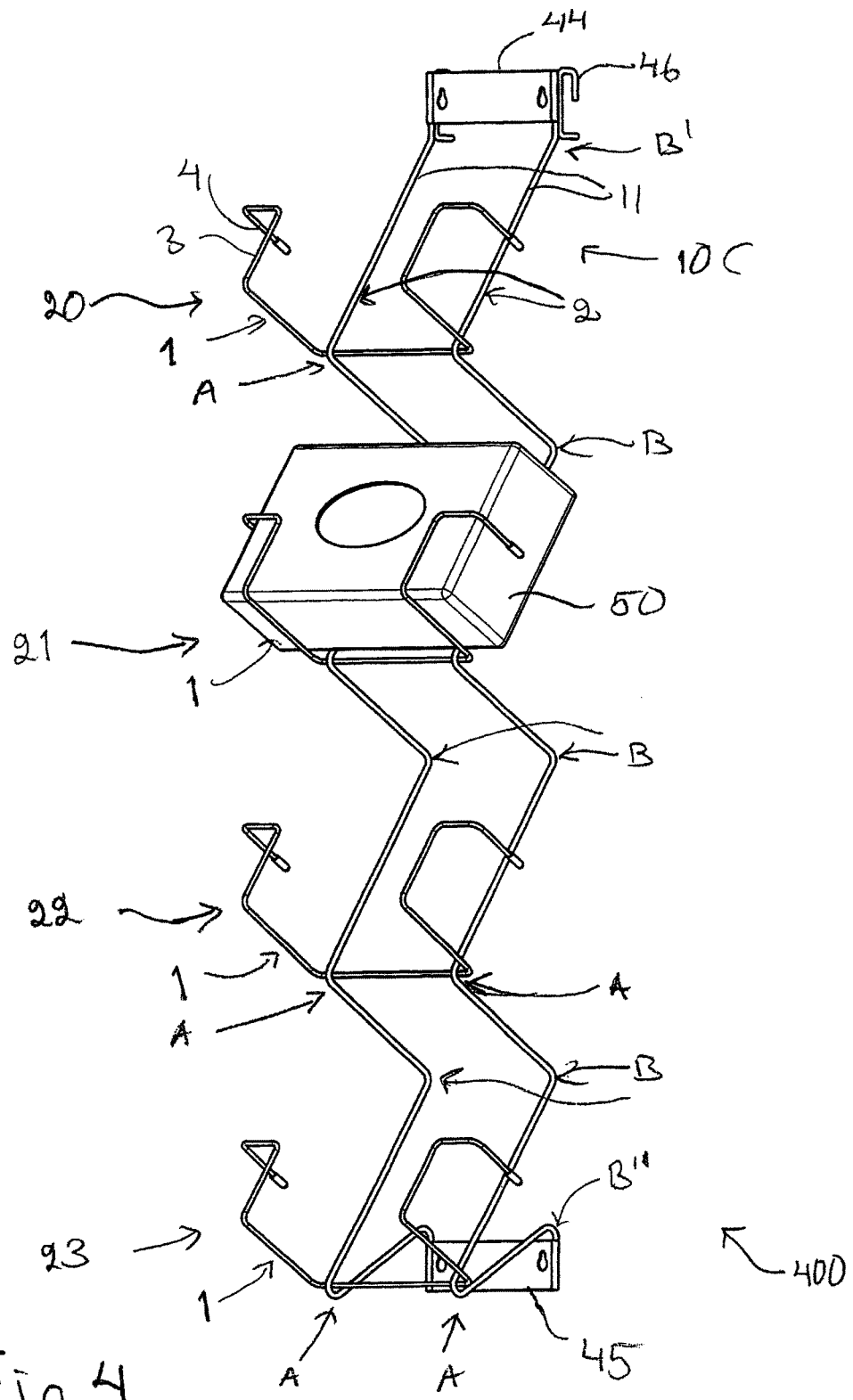
FIG. 4 shows an alternative embodiment of a holding arrangement.

In a manner corresponding to the manner shown in FIG. 4, a holding arrangement 400 which instead comprises a frame structure 10C with four holding elements 20, 21, 22, 23 is shown. In this embodiment the upper mounting element is a combined mounting element 44, 46. The holding arrangement according to the invention is not limited as far as the number of holding elements is concerned, but there may also be more.

Figure 5:
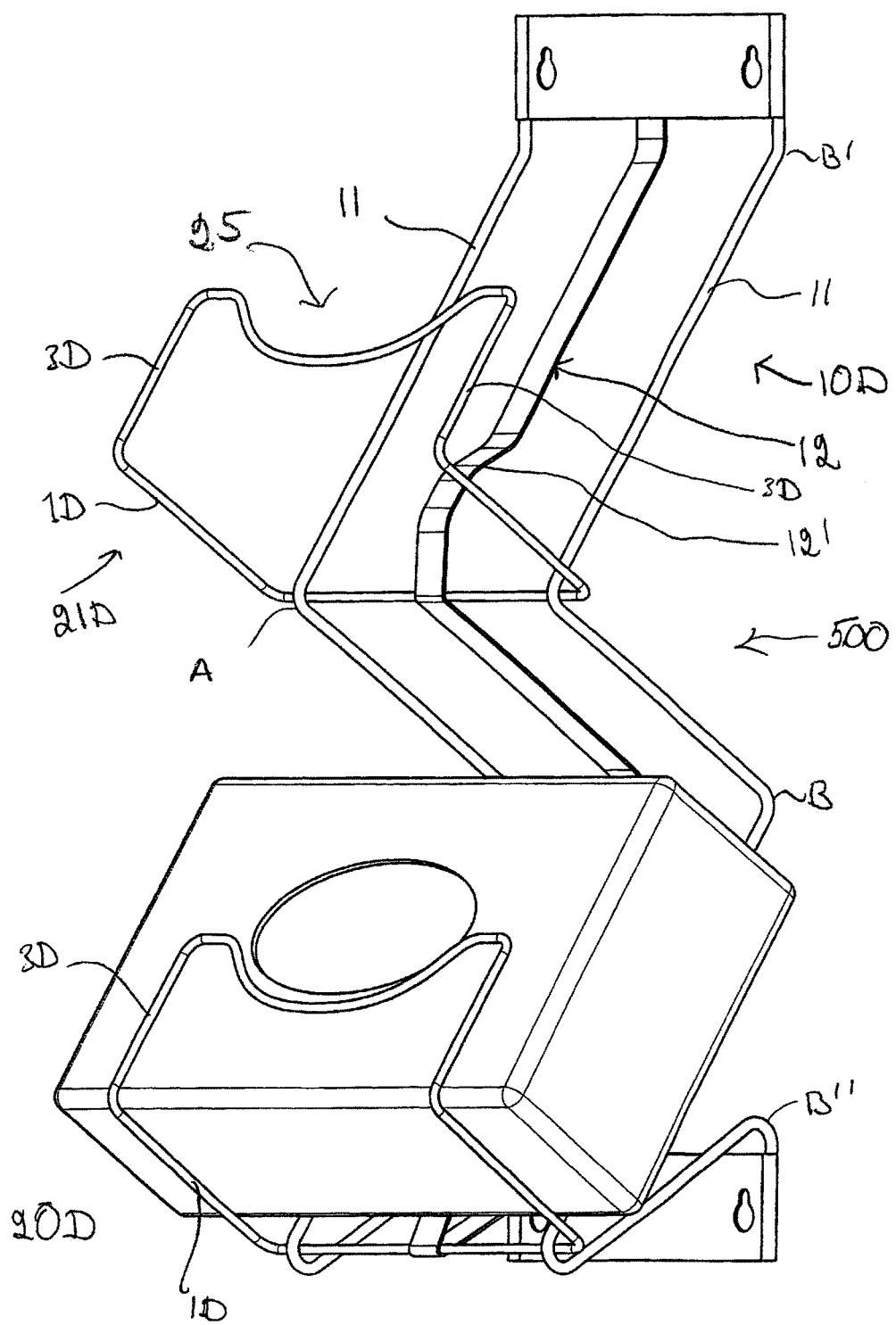
FIG. 5 shows a further alternative embodiment of the invention.

FIG. 5 shows a holding arrangement 500 wherein the frame structure 10D is provided with a rail 12 which extends in connection to the rear plane and which is formed to push 12' the packages towards the front support section so that the retaining capability is further improved, in particular in order to assure an ever better retaining capability when the packages merely contain as small number of articles, and thus have a lower weight and thus easier might fall out of the holding element 20D, 20D' when articles are withdrawn, even if the risk is low with a holding arrangement according to the invention and as described above.

The significance thereof may however be more important for example in embodiments in which no side support sections are used as is shown in FIG. 5.

It is however also possible to use a rail as an additional safeguard also in case side support sections are used (not shown).

Furthermore the front support section 3D shown in FIG. 5 is differently formed, with a front part, or a front branch section, which is connected by means of an intermediate semicircular section or a section which has the shape of a semi oval or any other appropriate form which for example can be shaped and adapted to surround the opening of an introduced package, which can be advantageous if additionally improved retaining capability in the front direction is desired, perpendicularly to the opening side, if a protection of the package material around a part of the opening or in the opening area is desired, or if certain surfaces are to have a good visibility. Since there are no sidesections, the flexibility as far as the width of the packages will be further increased.

Figure 6:
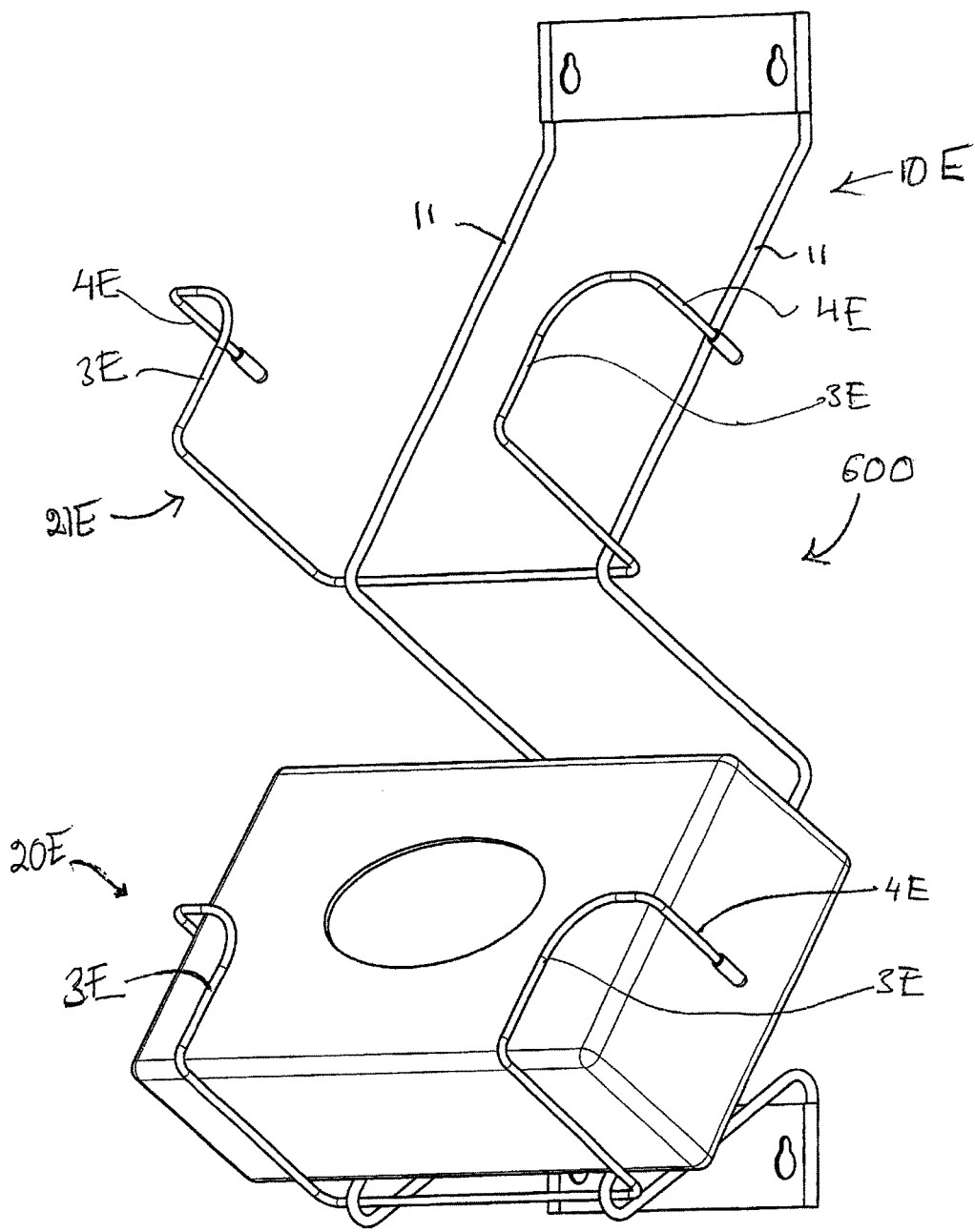
FIG. 6 shows another embodiment of a holding arrangement with a different holding element.

In FIG. 6 a holding arrangement 600 is shown which comprises a holding element wherein the front support sections 3E, 3E are formed by front frame sections which are angled with respect to the lower frame sections (alternatively, not shown, obliquely away from each other, outwards) sloping outwards towards a respective point where they are bent for example 90° and turn into the fourth frame sections which form side support sections 4E, 4E for respective holding elements.

Figure 7:
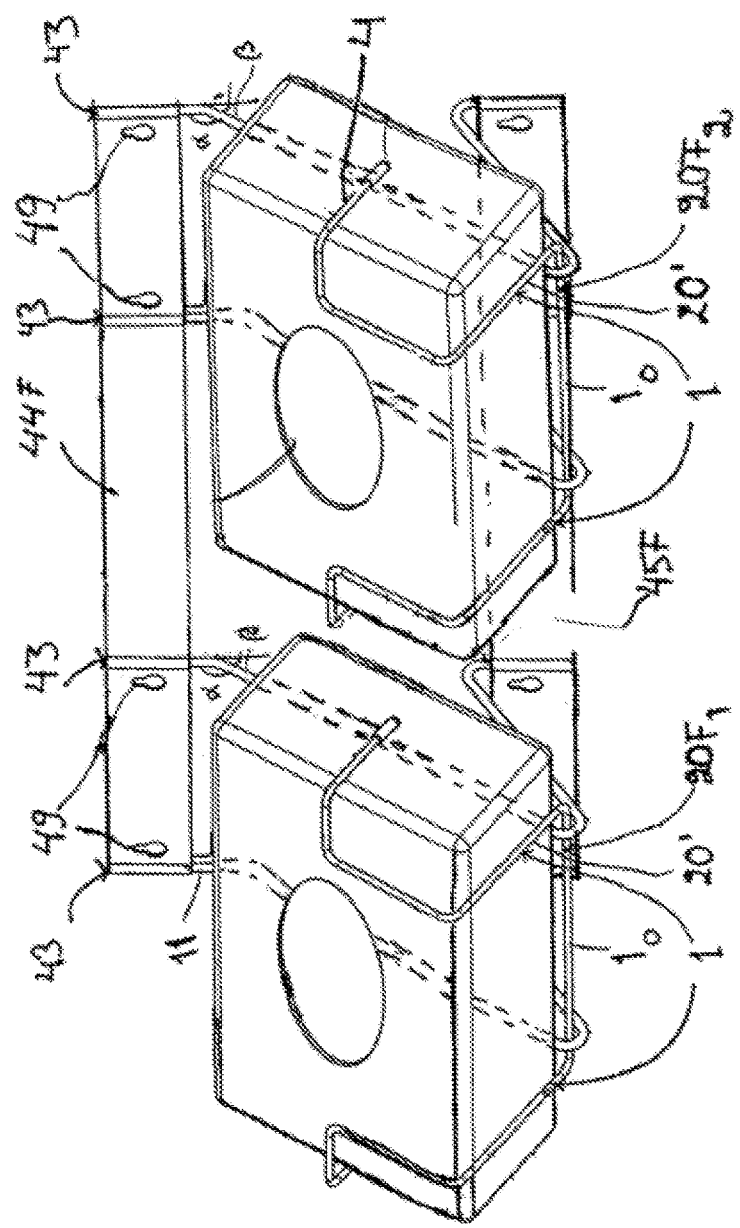
FIG. 7 shows further an alternative embodiment of a holding arrangement according to the invention.

In FIG. 7 a further alternative embodiment of a holding arrangement 700 is shown which is different from the holding arrangements described above in that it comprises upper mounting element 44F and lower mounting element 45F at which two or more holding elements 20F₁, 20F₂ can be arranged in parallel, fixedly or detachably, as in the above described embodiments. For example free, here denoted upper and lower, end portions or end sections of the frame elements can be fixedly or detachably arranged at the upper and lower mounting elements. In one embodiment they can be introducible in for that purpose dedicated grooves or guides 43 in the mounting elements, which after introduction can be mounted for example on a wall by means of screws or similar through for that purpose provided openings in the mounting elements 44F, 45F. In every other respect the holding arrangement can be formed in a number of different manners as described with reference to the other embodiments. It should be clear that different features in different embodiments freely can be combined and varied in any desired manner within the scope of the invention.

In alternative embodiments the holding elements can be formed in many different manners, they do not have to be made of wire shaped material, but they may also be formed by plate shaped material, cover entire sections, and they may also be formed as wire baskets or plastic holders or similar. They may also be attachably connectable to the frame structure, possibly with locking elements securing them in position or connectable by means of snap-in closure mechanisms or similar.

Also the frame structure can be differently formed and for example comprise band shaped elements, plate shaped elements or a plate shape or comprise in another displaceable telescopic elements so that the holding arrangement can be extended or shortened depending on need to comprise a larger or smaller number of holding elements.

It is an advantage of the invention that a secure retaining capability of packages in a holding arrangement is provided, as well as that access to articles is facilitated through the angled position, which makes the openings become extremely easy to access, which furthermore prevents other articles from falling out when an article is withdrawn.

It is also an advantage that a concept of holding arrangements is provided which is very flexible and which simply can be produced for different needs and depending on available space, for vertical mounting above each other as well as horizontally next to each other arranged of holding elements in any desired number.

The inclination also enables the arrangement of holding arrangements at a lower height as compared to known arrangements, since the articles are withdrawn obliquely upwards, which further, more is advantageous from an ergonomic point of view. Through its form the holding arrangements preferably are stackable which is advantageous both from a storing point of view and from a transportation point of view, and which therefore also provides for environmental advantages. If the production in addition thereto for example takes place from stainless steel, they can be recycled to a 100% which also is an environmental advantage.

Through its forming the holding arrangement further more is compact and only requires a small wall area when it is mounted on the wall as compared to known arrangements. It can also be provided with different types of mounting elements which enables mounting on trolleys, benches etc, and the inclination angle in any case provides for a simplified access to articles in the package. The mounting elements can be combined for different mounting options, or be dedicated for a particular kind of mounting.

If spring steel is used for the holding elements, further more an enhanced flexibility can be obtained, also in the depth direction, so that they therefore can be adapted for different types and sizes of packages.

The invention is of course not limited to the particularly illustrated embodiments, but it can be freely varied within the scope of the appended claims. If the holding elements are detachably arranged, it is also possible to, in one and the same holding arrangement, use holding elements for different dimensions of packages, for example for packages for disposable gloves and packages for masks, aprons or other one way articles which for example are kept in packages of different forms and/or sizes.

The invention claimed is:

1. An arrangement for holding product packages, comprising:
    a frame;
    at least one mounting element configured for substantially vertically mounting the frame; and
    at least one holding element configured for connection to the frame, each holding element comprising a first section configured to support, in a first plane, one side of a respective product package; a second section substantially perpendicular to the first section configured to support, in a second plane, a bottom side of the respective product package, the bottom side being opposite a top side of the respective product package having an opening; and a third section configured to support the top side of the respective product package, the third section extending substantially parallel to the second plane;
    wherein each holding element is configured to receive and retain a respective product package such that products or articles in the product package are accessible through the opening therein; the first plane forms an angle of substantially 90° with the second section; the second section forms an angle of at least 100° with a rear plane of the frame; the first section has a lower, inclined support section; the arrangement is configured for placing a respective product package in each holding element such that the top side of each product package is in an upwardly facing, outwardly sloping plane with respect to the rear plane or a vertical plane when the holding arrangement is mounted; the frame comprises at least two parallel frame elements having respective upper outer ends configured to connect to the at least one mounting element; the frame elements have zig-zag shapes with alternating sections between alternating rear support points and front turning or folding points; the rear support points form the rear plane and the front turning or folding points form a front plane substantially parallel to the rear plane; and a respective second section extends in a direction from the respective turning or folding point toward a rear support point located above the respective turning or folding point.

2. The arrangement of claim 1, wherein the frame elements are configured to connect to a separate lower mounting element either at a certain distance from the upper outer ends, or at respective lower ends of the frame elements; and the at least one mounting element is configured for at least one of wall mounting, bed mounting, and rim mounting.

3. The arrangement of claim 1, wherein the frame elements comprise metal wire.

4. The arrangement of claim 1, wherein the frame comprises a frame element of a band-shaped material, and at least an upper end of the frame element is either integral with a mounting element or is configured for connection to a mounting element.

5. The arrangement of claim 1, wherein each holding element further comprises additional side support sections arranged to delimit the respective holding element laterally and support additional sides of the respective product package.

6. The arrangement of claim 5, wherein a holding element comprises metal wire.

7. The arrangement of claim 1, wherein the second section forms an angle of between 120° and 160° with the rear plane of the frame.

8. The arrangement of claim 1, wherein at least two holding elements are mounted side by side in a horizontal direction on the frame, the frame comprises an extended frame structure or at least two frame structures, and the mounting elements include an integrated mounting element having an upper and lower portions or separate upper and lower mounting elements, and the mounting elements are configured for connection to the at least two holding elements.

9. The arrangement of claim 1, wherein the mounting element comprises upper and lower mounting elements for wall mounting.

10. The arrangement of claim 1, wherein the mounting element is configured for mounting on a rail or ramp of intensive-care equipment.

11. The arrangement of claim 1, wherein the at least one holding element comprises at least one of a metal-wire basket, a plastic basket, and a holding element having closed-wall second or rear section.

12. An arrangement for holding product packages, comprising:
a frame;
at least one mounting element configured for substantially vertically mounting the frame; and
at least one holding element configured for connection to the frame, each holding element comprising a first section configured to support, in a first plane, one side of a respective product package; a second section substantially perpendicular to the first section configured to support, in a second plane, a bottom side of the respective product package, the bottom side being opposite a top side of the respective product package having an opening; and a third section configured to support the top side of the respective product package, the third section extending substantially parallel to the second plane;
wherein each holding element is configured to receive and retain a respective product package such that products or articles in the product package are accessible through the opening therein; the first plane forms an angle of substantially 90° with the second section; the second section forms an angle of at least 100° with a rear plane of the frame; the first section has a lower, inclined support section; the arrangement is configured for placing a respective product package in each holding element such that the top side of each product package is in an upwardly facing, outwardly sloping plane with respect to the rear plane or a vertical plane when the holding arrangement is mounted; each holding element further comprises additional side support sections arranged to delimit the respective holding element laterally and support additional sides of the respective product package; a holding element comprises a bent metal wire having two parallel side branches and an interconnecting branch that interconnects the side branches and extends in an outer side of the second plane, the two side branches comprise first branch sections that extend in the first plane and form the first section, a second branch section having an angle of substantially 90° with respect to the first branch sections and extending in a plane formed by the third section, and a third branch section inclined and extending substantially parallel to the rear plane and forming the side support sections; the frame comprises at least two parallel frame elements having respective upper outer ends configured to connect to the at least one mounting element; the frame elements have zig-zag shapes with alternating sections between alternating rear support points and front turning or folding points; the rear support points form the rear plane and the front turning or folding points form a front plane substantially parallel to the rear plane; and a respective second section extends in a direction from the respective turning or folding point toward a rear support point located above the respective turning or folding point.

13. The arrangement of claim 12, wherein the third branch section of each holding element comprises free outer ends that end in, or adjacent, respective side support sections forming side support planes.

14. The arrangement of claim 13, wherein the side support sections are elastic, thereby accommodating different product package widths.

15. The arrangement of claim 12, wherein respective third branch sections of a holding element are parallel to a respective first branch element of the holding element or form an angle of at least 90° with the first branch element.

16. The arrangement of claim 12, wherein respective first branch sections of a holding element form an acute angle with and approach each other in a direction from the second section, and third branch sections slope outwardly and obliquely until they reach a point where they are angled and turn into respective third frame sections.

17. An arrangement for holding product packages, comprising:
a frame;
at least one mounting element configured for substantially vertically mounting the frame;
at least one holding element configured for connection to the frame, each holding element comprising a first section configured to support, in a first plane, one side of a respective product package; a second section substantially perpendicular to the first section configured to support, in a second plane, a bottom side of the respective product package, the bottom side being opposite a top side of the respective product package having an opening; and a third section configured to support the top side of the respective product package, the third section extending substantially parallel to the second plane; and
a spring plate arranged substantially parallel to the frame and configured to exert pressure against the bottom of a respective product package disposed in a holding element;
wherein each holding element is configured to receive and retain a respective product package such that products or articles in the product package are accessible through the opening therein; the first plane forms an angle of substantially 90° with the second section; the second section forms an angle of at least 100° with a rear plane of the frame; the first section has a lower, inclined support section; the arrangement is configured for placing a respective product package in each holding element such that the top side of each product package is in an upwardly facing, outwardly sloping plane with respect to the rear plane or a vertical plane when the holding arrangement is mounted; the frame comprises at least two parallel frame elements having respective upper outer ends configured to connect to the at least one mounting element; the frame elements have zig-zag shapes with alternating sections between alternating rear support points and front turning or folding points; the rear support points form the rear plane and the front turning or folding points form a front plane substantially parallel to the rear plane; and a respective second section extends in a direction from the respective turning or folding point toward a rear support point located above the respective turning or folding point.

* * * * *